United States Patent
Wright (10) Patent No.: US 7,274,456 B2
(45) Date of Patent: *Sep. 25, 2007

(54) NON-DESTRUCTIVE SINGLE SEED OR SEVERAL SEEDS NIR ANALYZER AND METHOD

(75) Inventor: Steven L. Wright, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 351 days.

This patent is subject to a terminal disclaimer.

(21) Appl. No.: 10/843,842

(22) Filed: May 12, 2004

(65) Prior Publication Data

US 2005/0254053 A1      Nov. 17, 2005

(51) Int. Cl.
*G01N 21/00* (2006.01)
*G01J 5/02* (2006.01)

(52) U.S. Cl. ............. 356/432; 250/339.11; 250/339.12

(58) Field of Classification Search ............. 250/339.1, 250/339.11, 339.12
See application file for complete search history.

(56) References Cited

U.S. PATENT DOCUMENTS

| 4,692,620 A | 9/1987 | Rosenthal et al. |
| 5,751,421 A | 5/1998 | Wright |
| 5,991,025 A | 11/1999 | Wright |
| 6,483,583 B1 | 11/2002 | Wright |
| 6,646,264 B1 | 11/2003 | Modiano |
| 2003/0168600 A1* | 9/2003 | Tseng et al. ........... 250/339.07 |

FOREIGN PATENT DOCUMENTS

| EP | 1 046 902 A2 | 10/2000 |
| WO | WO 00/04349 A1 | 1/2000 |
| WO | WO 02/25247 A2 | 3/2002 |
| WO | WO 02/25247 A3 | 3/2002 |
| WO | WO 02/48687 A2 | 6/2002 |
| WO | WO 02/48687 A3 | 6/2002 |
| WO | WO 2004/079346 A1 | 9/2004 |

OTHER PUBLICATIONS

Baye et al., "Analyzing Seed Weight, Fatty Acid Composition, Oil, and Protein Contents in *Vernonia galamensis* Germplasm by Near-Infrared Reflectance Spectroscopy", JAOCS, 81(7):641-645 (2004).
Cogdill et al., "Single-Kernel Maize Analysis by Near-Infrared Hyperspectral Imaging", PITTCON 2002 description—1 page.

(Continued)

*Primary Examiner*—Gregory J. Toatley, Jr.
*Assistant Examiner*—Amanda H Merlino
(74) *Attorney, Agent, or Firm*—McKee, Vorhees & Sease, P.L.C.

(57) ABSTRACT

A method and apparatus for optically interrogating a particle comprising obtaining a plurality of optical interrogations from a plurality of orientations relative the particle. In one aspect, the particle is tumbled relative to optical interrogation direction and reflected or transmitted energy is collected and added into a single spectrum that represents a complete spectral composition of the sample.

36 Claims, 6 Drawing Sheets

OTHER PUBLICATIONS

Cogdill et al., "Single-Kernel Maize Analysis by Near-Infrared Hyperspectral Imaging", Transactions of the ASAE, 47(1):311-320 (2004).

Delwiche et al., "Classification of Wheat by Visible and Near-Infrared Reflectance from Single Kernels", Cereal Chemistry, 73(3):399-405 (1996).

Shadow et al., "Practical Single-Kernel NIR/Visible Analysis for Small Grains", Cereal Foods World, 45(1):16-18 (2000).

Velasco et al., "Estimation of seed weight, oil content and fatty acid composition in intact single seeds of rapeseed (*Brassica napus* L.) by near-infrared reflectance spectroscopy", Euphytica 106:79-85 (1999).

* cited by examiner

NON-DESTRUCTIVE SINGLE SEED OR SEVERAL SEEDS NIR ANALYZER AND METHOD

BACKGROUND OF THE INVENTION

A. Field of the Invention

The present invention relates to analyzing individual particles, such as seeds, tablets, pellets, and the like, for quantitative measure of one or more chemical components, constituents, or characteristics. One exemplary application is to agricultural seeds, such as corn and soybeans, to investigate various quality traits including, but not limited to, moisture, protein, oil, starch, amino acids, fatty acids, phytate, and other traits of interest.

B. Problems in the Art

The advantages of gaining knowledge of the chemical components or other traits of agricultural crop seed are well known and well documented. Plant breeding or plant genetic experiments use such an analysis. As such, experiments become more sophisticated, more complete and accurate information is desirable. This includes the ability to obtain information about single seeds.

One conventional evaluation technique grinds the seed up into, hopefully, a homogenous powder. Any of a variety of laboratory techniques can then be utilized to derive information about the chemical make-up of the powder. Information can be collected and used. As can be appreciated, this method is destructive of the seed. Additionally, significant time and resources are required to grind and handle individual seed and its powdered form.

Near infrared spectroscopy is a well-known science for interrogating substances for chemical makeup. It directs electromagnetic energy in the near infrared (NIR) spectrum at a specimen and detects the transmittance and/or reflectance of that energy. Evaluation of absorption of the energy reveals chemical makeup of the portion of the specimen interrogated.

Use of NIR to evaluate agricultural grain is also well known. See for example, U.S. Pat. Nos. 5,751,421; 5,991,025; and 6,483,583 to Wright et al. and incorporated by reference herein. However, those patents speak to analyzing seed or grain in bulk quantity with non-destructive NIR techniques. One example rotates a bulk sample of many seeds over an optical window. There can be agitation of the bulk sample, but not at the location of the optical window and not while taking the optical sample. The optical sampling is therefore from one plane. There is a need to analyze particles in less than bulk quantities, including individually. The main problem associated with single seed or several seeds analysis is the difficulty of complete optical interrogation of the sample. A corn kernel, for example, is very heterogeneous. That is, its major components are somewhat compartmentalized. The starch is primarily found in the endosperm, while the protein and oil are mostly contained in the germ. Manual handling of single or several seeds is not satisfactory. It is too cumbersome and time consuming, and is subject to erroneous readings. This problem has been recognized in the art and attempts have been made to solve it. Other types of seed and other types of particles can be heterogeneous.

For example, single seed analyzers utilizing NIR are commercially available. One device (Brimrose; Baltimore, Md. USA, Model # Luminaire 3076 "Seed Meister" NIR Analyzer) moves single seeds on a moving belt past an NIR transmitter. A detector captures reflectance or transmittance of the NIR energy which is then analyzed. By appropriate control, the individual seeds can be serially presented and analyzed. While this method optically samples each kernel, it does so from basically one direction (or in generally one plane), and for a limited window in time.

Another prior art method directs NIR energy into a single seed from various directions while the seed is placed or laid in a hole. This increases the number of interrogation angles, but is still generally in a single plane. The supporting structure holding the seed also blocks parts of the seed from optical interrogation, as the seed is static in the hole.

Therefore, a real need in the art exists for a method which provides a better optical sample of the whole particle under investigation in a non-destructive, efficient, economical manner.

BRIEF SUMMARY OF THE INVENTION

It is therefore a principle object, feature, aspect and/or advantage of the present invention to provide an apparatus and method for NIR analysis of single or several particles which improves over or solves problems and deficiencies in the art. Further objects, features, aspects, and/or advantages of the present invention include an apparatus and method as above described which:

a. optically samples from a plurality of directions and materially different planes, b. has rapid sampling, c. collects a substantial amount of transmitted NIR energy for evaluation by transmittance and/or reflectance, d. is non-destructive, e. can provide an aspect of randomness regarding sampling orientation, f. can be used in a wide range of multi-varied analysis of the particle, g. promotes improved accuracy of analysis, h. is adaptable to a variety of different applications and particles, including particles of different sizes, shapes, heterogeneity, types, and measurements, i. is relatively economical, j. is relatively efficient, k. is relatively durable.

A method according to the present invention includes optically sampling a single particle from a plurality of directions in different planes. The optical sampling is used to evaluate chemical components or other characteristics of the particle. This can be accomplished by rotating the particle relative to the direction of sampling, rotating the direction of sampling relative the particle, or both. In another aspect of the invention, the particle is substantially suspended or exposed to the optical sampling from numerous directions.

In another aspect of the invention, a plurality of particles are optically sampled in this manner. The plurality of particles is preferably several, meaning not a bulk sample of tens of particles.

In a still further aspect of the invention, particles are agricultural grain, including corn and soybeans, and the chemical components analyzed relate to various quality traits of such agricultural seed.

An apparatus according to the invention includes an optical sampling collector that defines an optical sampling location. A single particle can be positioned in the optical sensing location. The optical sampling collector allows optical sampling from a plurality of directions in different planes and from different locations of the particle. The apparatus can, in one aspect, include a mechanism to induce change in orientation of the particle relative to collection direction. One aspect of such an apparatus would include an air jet operatively positioned to promote change in orientation of the particle. In another aspect of the invention, the collector can be operatively connected to a mechanism that changes orientation of the collector relative to the particle. In a further aspect of the invention the particle and the direction of collection of the collector can be changed. In a further aspect of the invention, the apparatus can analyze a plurality of particles.

DETAILED DESCRIPTION OF THE PREFERRED EMBODIMENT

A. Overview

For better understanding of the invention, a more detailed description of a specific exemplary embodiment of the present invention will now be set forth. It is to be understood this is but one form the invention can take and is not by way of limitation, but rather an example of one of many forms the invention can take.

Frequent reference will be taken to the appended drawings. Reference numbers and letters will be used to indicate certain parts and locations in the drawings. The same reference numbers will be used to indicate the same parts and locations in the drawings unless otherwise indicated.

B. General Environment of Exemplary Embodiment

The first exemplary embodiment will be described with regards to evaluation of single kernels of agricultural crop, and for illustration only, corn seed. The invention will be described in the context of optical interrogation of individual corn kernels using near infrared (NIR) electromagnetic energy for the purposes of use in a plant breeding program or genetically modified plant advancement program. Individual kernels are from known origin. For example, the user of the present system has, or is given, information about the parentage or history of the seed.

C. General Diagram of Sampling Probe

Figure 1:
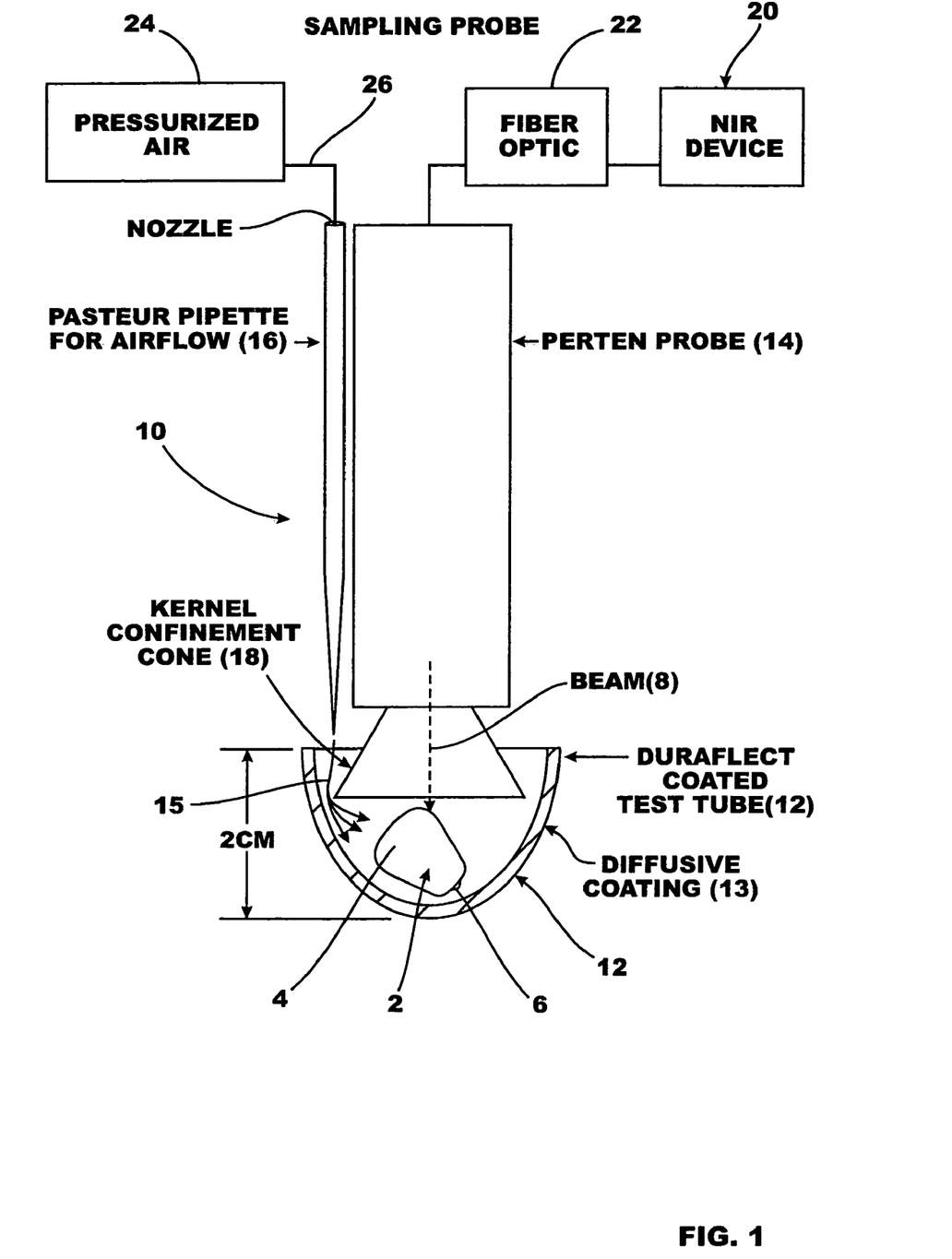
FIG. 1 is a diagrammatic view of a sampling probe according to an exemplary embodiment of the present invention, and diagrammatically showing connections to other components useful for a sampling system.

FIG. 1 illustrates, in diagrammatic form, a concept for a sampling probe 10 for optical interrogation of a single kernel 2 of maize or corn. As is indicated in FIG. 1, corn seed has a heterogeneous makeup. Most of the starch is found in endosperm 4. Protein and oil are mostly contained in germ 6. Endosperm 4 and germ 6 are highly compartmentalized.

Kernel 2 is placed in a cup 12 having a curved inner surface with a diffuse or specular reflective coating 13. In one embodiment, cup 12 is a Duraflect™ coated bottom portion of a conventional test tube with an open top cut to the size shown. Duraflect is a diffuse reflectance white coating available from Labsphere, Inc. North Suttan, N.H. USA. It can be applied in a number of ways, including, but not limited to, spraying, painting, sputtering, and dipping. Other coatings could be used, either inside or outside the transparent cup (although absorbance band issues could arise if placed outside). One example of an alternative diffuse coating 13 is Avian "D" coating available from Avian Technologies of Helsinki, Finland. Other reflective coatings such as gold could also be used. The coating could be placed on the inside or outside of the sample cup. Other types, configurations, and materials for cup 12 could be used. One example of a transparent or partially transparent material is sapphire, which might have better optical qualities than ordinary test tube glass. One example is a cup formed of non-transparent material is hardened aluminum but with an interior diffuse or specular reflective coating. In another embodiment, the sample cup could be constructed from a reflective material such as gold, aluminum or spectralon.

A probe sheath or head 14 includes fiber optics or other components to both transmit NIR energy out its lower end in the direction of kernel 2, as well as receive reflected electromagnetic energy. Probe head 14 includes a kernel confinement cone 18 at its distal or bottom end. Cone 18 is basically a conical member with a hollow interior and opposite open ends. It extends from the bottom of probe sheath 14 and increases in diameter such that the diameter of its open distal end approaches the inside diameter of cup 12 when probe 14 is in operative position. Cone 18 functions to physically retain kernel 2 in cup 12 during operation of the system and in the general path of NIR energy from probe 14. The inner walls of cone 18 converge at approximately 25° collection angle or cone of acceptance of head 14.

Probe head 14 is part of a larger NIR analyzer such as are well known in the art and available commercially. In this embodiment, probe head 14 is operatively connected by fiber optics 22 to an NIR processor. In particular, the entire NIR analyzer is a commercially purchased DA7000 model from Perten Instruments, Huddinge, Sweden. Another example is a Perten Instruments DA7200 system. It is a stand alone system with integrated computer software and can be operated to generate NIR energy of desired wavelengths, transmit them through fiber optic 22 (e.g. bifurcated cable) and probe 14 and out and through cone 18, and collect reflected NIR energy, direct it through a fiber optic 22 back to device 20 where it can be recorded and analyzed. Some calibration and setup is required.

As previously mentioned, however, the art and science selecting NIR energy, transmitting it to an item under analysis, collecting reflected or transmitted NIR from the object under analysis, and recording and processing collected NIR energy, is well known in the art, as well as operation of such machines. It therefore will not be described further.

Probe 10 also includes a conduit to deliver pressurized air to the interior of cup 12. One example, diagrammatically illustrated in FIG. 1, is a Pasteur pipette 16 mounted longitudinally along probe head 14. The distal end of pipette 16 has a constricted opening that is aligned generally near the bottom of probe head 14 in a manner such that pressurized air will enter cup 12 in a gap between the outside of cone 18 and the inside of cup 12. The opposite end of pipette 16 is operatively connected to a tube or hose 26 which is in fluid communication with a pressurized air source 24.

Figure 2:
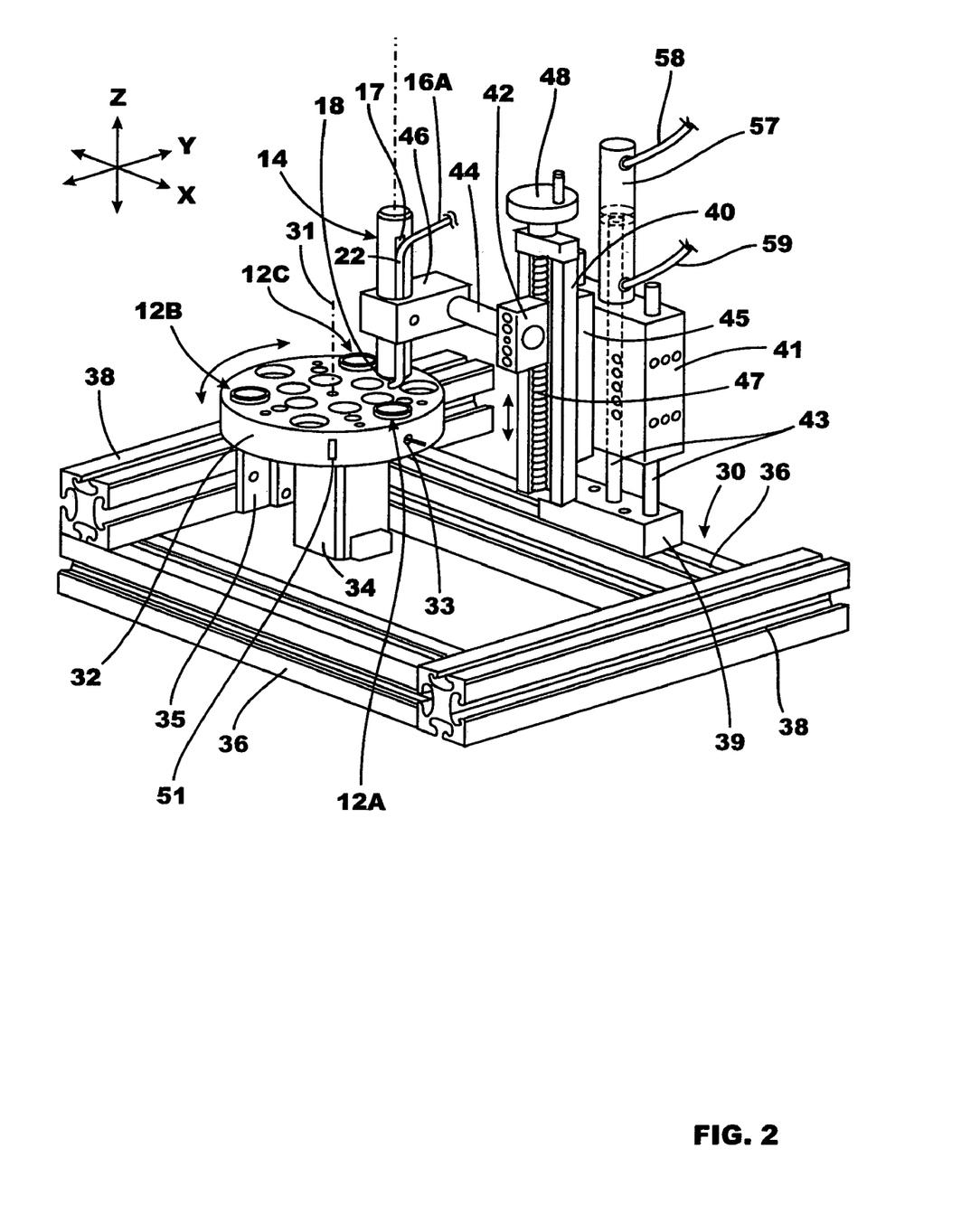
FIG. 2 is a partial, simplified perspective view of the sampling probe of FIG. 1 implemented with a programmable indexer for automated or semi-automated sampling.
Figure 3:
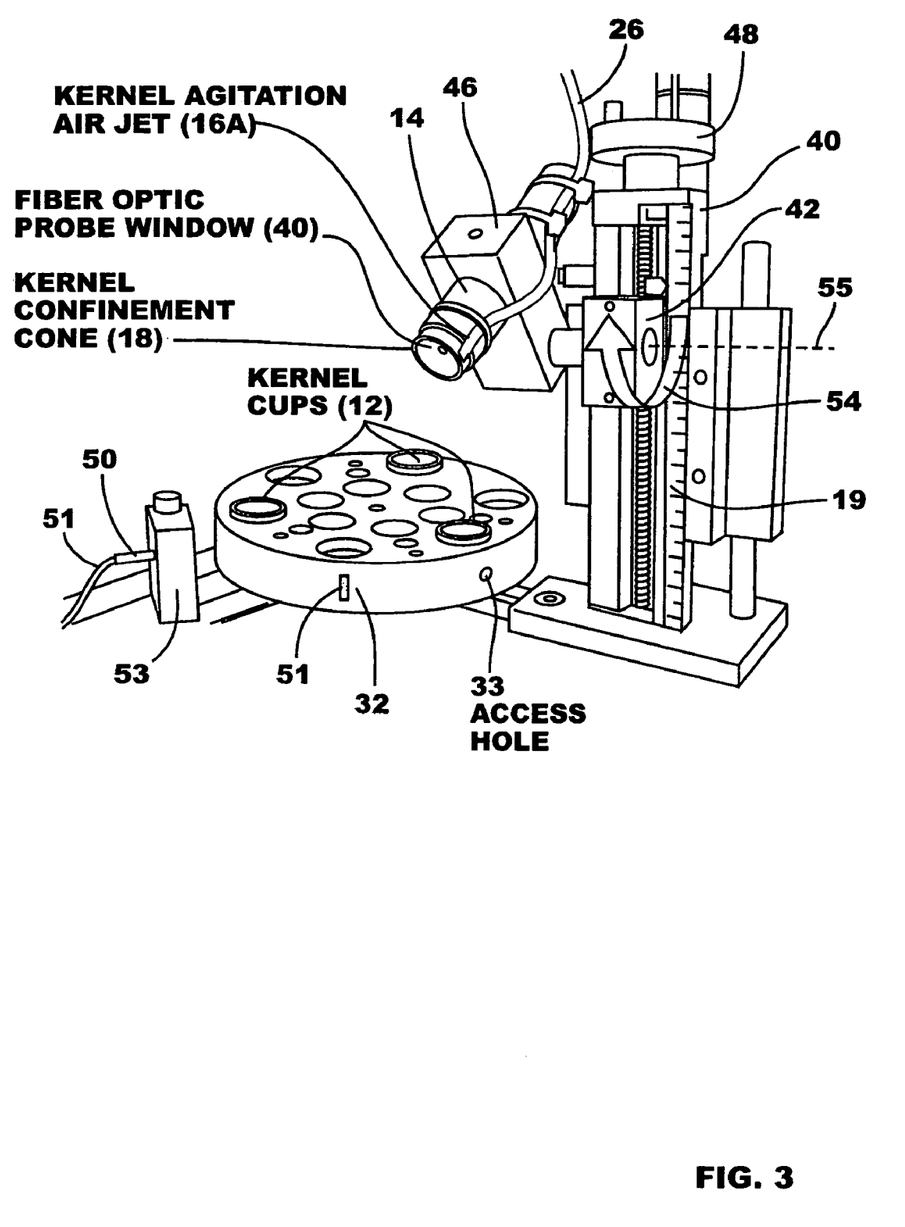
FIG. 3 is a perspective view, primarily of the sampling probe and indexable turntable, but illustrating a further degree of freedom of movement of part of the probe.
Figure 4:
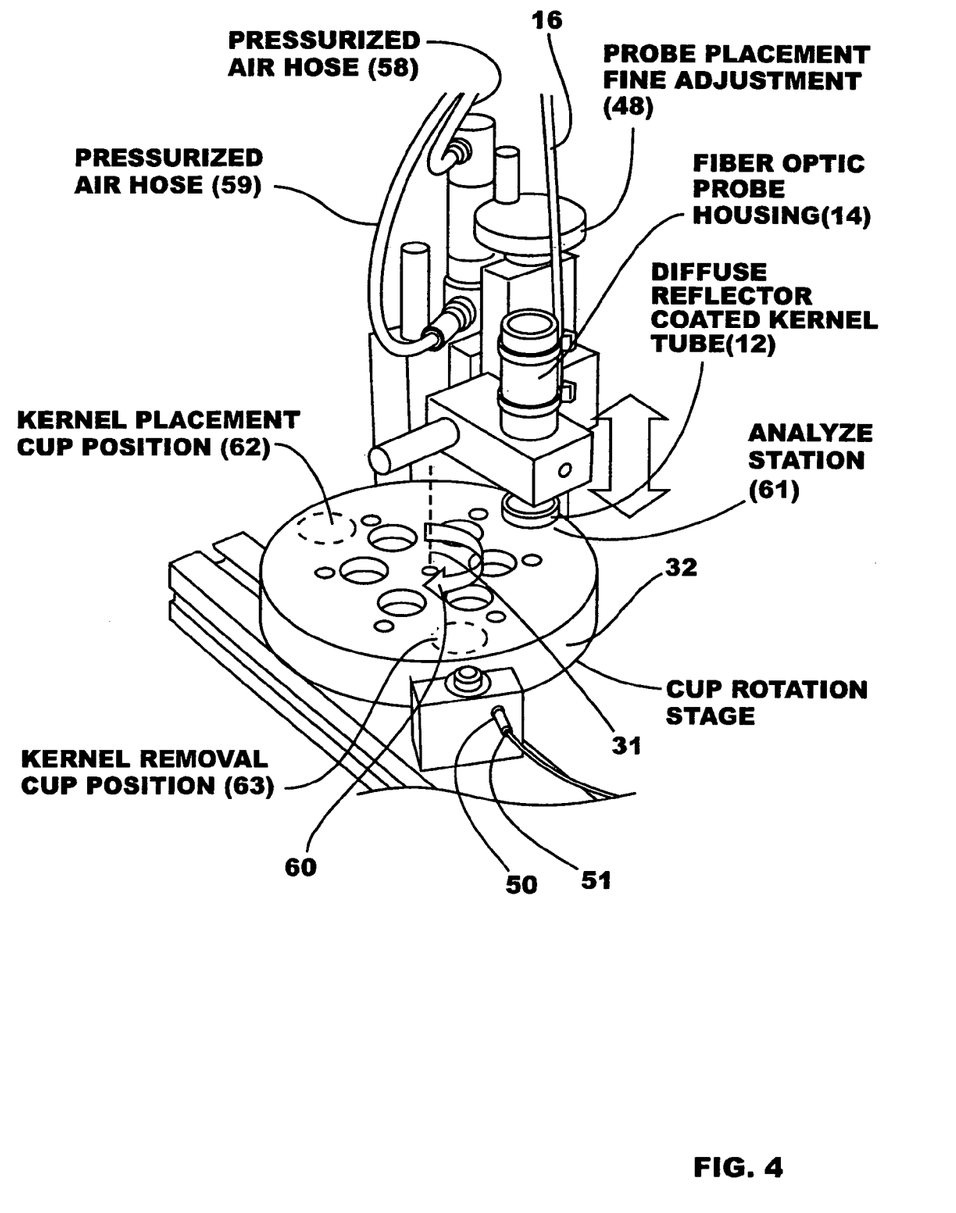
FIG. 4 is a perspective view of primarily the sampling probe and indexable turntable and illustrating functional aspects of the probe.

Instead of a pipette such as is shown in FIG. 1, conduit 16 could comprise a stainless steel tube or catheter 16A can be used (see, e.g., FIGS. 2-4). Tube 16A could be directly connected to a pressurized air source. Other conduits or ways to generate perturbation of a seed in cup 12 are, of course, possible.

The combination of components 24, 26 and 16 essentially create a small air jet 15 from conduit 16. When probe 14 is in the position shown in FIG. 1, the air jet 15 would be directed towards the left hand inside surface of cup 12 and towards kernel 2, which would be laying in the bottom of cup 12. Cup 12 can be generally hemispherical in shape and surround kernel 2. The amount of air pressure from air jet 15 would be selected to provide enough force to tumble kernel 2 in the general position shown in FIG. 1. Cone 18 would ensure the kernel would not move outside cup 12. By appropriate operation of NIR device 20, optical interrogation of random orientations of kernel 2 would occur because of the continuous tumbling of kernel 2. Collection of reflectance from nearly every possible kernel orientation would be acquired and co-added into a single spectrum that represents the complete spectral composition of the sample, here kernel 2.

As can be appreciated, the nature of the air jet should be enough to tumble kernel 2 but not push it up against the right side of cup 12. Confinement cone 18 is designed to assure kernel 2 stays in the general cone of acceptance (the beam of NIR energy from probe head 14), but allows the pressurized air from conduit 16 to effect kernel 2. The air jet should be enough to cause a continuous or substantially continuous random tumbling of kernel 2, and not a sporadic sliding or minimal movement, such that almost every possible kernel orientation is acquired. Force of the air jet can be selected from empirical testing as corn kernels have a fairly known range of size, shape and configuration, at least regarding those that are candidates to be tested for purpose of plant advancement experiments. For example, by observation, pressurized airflow from conduit 16 could be adjusted from initially no air flow until substantially continuous tumbling of an average sized kernel 2 is created. The goal would be to produce substantially continuous tumbling. Airflow could then be increased until the kernel is pushed away or otherwise shoved to the side in cup 12, which would be undesirable. Airflow could then be adjusted back down to a level that would work for most kernels to create the substantially continuous tumbling but keep the kernel centered in cup 12. Of course, different air delivery systems, pressures, and configurations could result in different air pressures or arrangements to effect a substantially continuous reorientation of the kernel in the energy beam, and the appropriate or desired airflow could be empirically derived.

A diffuse or specular coating 13 such as previously described can assist in (a) directing NIR energy from probe head 14 to kernel 2 and (b) collecting reflected NIR or NIR transmitted through kernel 2 into probe 14. As mentioned, coating 13 can be one that is commercially available and, for NIR transparent cups 12 can be placed on the exterior or interior of cup 12. The range of specularity versus diffusiveness can be selected. It has been found that a diffusive coating may not be necessary for satisfactory operation relative to deriving chemical components of the kernel. It is believed that a highly reflective surface may be as or more valuable. A highly reflective surface would tend to keep all the light inside cup 12.

However, it should be noted that a corn kernel, for example, itself is light diffusive externally. Therefore, it is believed that even a transparent cup 12, with no coating, would produce satisfactory results. NIR energy would reflect diffusively from the kernel. Therefore, as the kernel tumbled in cup 12, collection of the energy would have a randomness as described earlier.

A diffuse and highly reflective coating can be advantageous, as will be explained in more detail later, relative to deriving certain characteristics of the particle. An example of a highly reflective but diffuse coating would be sputter-coated diffuse gold placed on the exterior or interior of cup 12.

Thus, the sampling probe 10 of FIG. 1, including essentially a retainer for a single kernel 2, an actuator to induce rotation or tumbling of kernel 2 in the retainer, and a probe head adapted to bathe the kernel in NIR and collect reflectance, provides an apparatus and method for optical interrogation of a single kernel from many, if not almost all, orientations. No major modification is needed to the NIR analyzer or probe head. Components to retain and tumble the kernel are not complex or expensive. Yet the multiple interrogation orientations are generated without the work or having to manually move the particle or any part of the apparatus.

NIR analyzers of the type mentioned can quickly acquire satisfactory reflectance for processing. Normally a second or less of collection is adequate. A collection for longer, but still relatively short periods (e.g. 10 seconds), is believed to assuredly obtain a complete interrogation. However, in situations where a comparison of limited number of chemical components or particle characteristics is required and there is a sensitivity to that inquiry, times as fast as the limits of the machine should work (e.g. 30 microseconds or μs).

D. Positioner for Sampling Probe

A set-up like illustrated in FIG. 1 could be used to optically sample a particle or seed. However, FIGS. 2-4 show a positioner apparatus that allows sampling probe 10 to be automated or semi-automated relative to its operation. It allows a cup 12 with a seed to be automatically rotated into position for optical sampling analysis, probe 10 moved down into operational position relative cup 12, and then the optical sampling to take place. It then can automatically or semi-automatically move probe 10 away and rotate the seed that was optically sampled to a position it can be removed from cup 12. The process can then efficiently repeat for succeeding seeds.

What will be called positioner 30 includes a rotatable turntable 32 having multiple (here three) cups 12 A, B, and C positioned in the upper face of turntable 32. As can be seen, additional cups 12 (including different sizes), could be installed into turntable 32 into the additional available cup holes, if desired. Or, only one cup could be used.

Turntable 32 has an axis of rotation indicated by line 31 in FIG. 2. Turntable 32 is rotatably mounted on an axle (not shown) aligned along axis of rotation 31. The axle extends from turntable motor 34 (e.g. stepper motor) which is mounted to rail 38 by mount 35.

There is an opening 33 in the side of turntable 32 aligned with each cup 12 to allow some radial access to cup 12.

A ferromagnetic metal strip or sliver 52 is mounted to the outside of turntable 32. An appropriate magnetic detector 50 (e.g. magnetic proximity detector) such as are well-known and commercially available can be mounted in mount 53 fixed near the side of turntable 32 (see FIG. 3). Detector 50 would trigger when metal sliver 52 is aligned with the photodiode. By appropriate placement of metal sliver 52 and detector 50, detector would sense when cup 12 is in a "home" position, e.g. when it is directly under probe 10 (e.g. the analyze station or position 61 in FIG. 4). This arrangement can be used to allow the system to know when a cup 12 is in correct alignment with probe head 14.

The two sets of parallel, spaced-apart rails 36 and 38 basically define a framework for the operational components of positioner 30. Rails 36 and 38 would be connected in a fixed relationship. Left-most rail 38 in FIG. 2 supports turntable 32 and its motor 34 by mount 35 in a selected fixed position along rail 38 (by screws, bolts, or other methods, or by some releasable mechanism, e.g. clamp) in what will be called the "y" direction.

A vertical tower 40 is mounted to the right-most rail 36 in FIG. 2 by mount 39, again in a selected, fixed position. Tower 40 supports probe 10, but also facilitates some automated movement of probe 10 relative to turntable 32 in what will be called a "z" direction, as described below.

It is to be understood, however, that the position of turntable 32 along rail 38 can be fixed as can the position of tower 40 along rail 36, such that probe head 14 would be aligned along a vertical axis that correspond generally with the center of each cup 12 on turntable 32. In essence, in operation all that would need to be moved would be probe head 14 from a position as shown in FIG. 2 above a cup 12, to a position such as shown in FIG. 1, with confinement cone 18 of probe head 14 into cup 12, and rotation of turntable 32, when probe head 14 is in the raised position of FIG. 2, to allow insertion and removal of a kernel from the cup 12.

In the embodiment, the system is operated such that only one cup 12 is utilized. It is rotated in one direction to allow a kernel to be placed into cup 12, rotated to the interrogation or analysis station shown in FIG. 2, and then rotated in a different direction to a seed removal station after interrogation is complete. However, a plurality of different specimen containers (cups 12) can be presented to a stationary probe 14 and/or probe 14 could be moved to any one of specimen containers.

Three vertical posts 43 fixed in mount 39 support pneumatic linear slide drive 41, which slides vertically up or down on posts 43. An internal piston in two-way pneumatic cylinder 57 is fixedly connected to middle post 43. Depending on whether pressurized air is delivered to hose 58 or 59, slide drive moves down or up respectively.

What will be called micro-positioner 40 is mounted to the side of slide drive 41 by connection 45. A carriage 42 is movable vertically along micro-positioner 40 by manual rotation of knob 48. A probe block 46, which holds probe sheath 14, is attached to carriage 42 by arm 44. Probe block 46, and thus probe sheath 14, can pivot upwardly over an angular range around the longitudinal axis of arm 44, as indicated by the arrow in FIG. 3.

The above-described arrangement of tower 40 allows what will be called macro-adjustment by linear slide drive 41 and micro-adjustment by micro-positioner 40. The macro-adjustment is automated in the sense an intelligent controller could instruct pneumatic linear slide drive to move relatively larger distances. Micro-adjustment is here manual (but could be automated) by an operator rotating knob or handle 48 which turns threaded rod 47 which in turn moves z-block 42 up or down. The threads on rod 47 are selected so that travel of z-block 42 is relatively small for each rotation of knob 48. This "micro adjustment" for vertical position of probe 14 allows for very precise up and down movement of cone 18 and probe 14 relative to cup 12.

FIG. 2 illustrates, instead of a pipette such as is shown in FIG. 1, a stainless steel tube or catheter 16A extended along probe 14 as the conduit for pressurized air to cup 12. Its distal end could be positioned adjacent or just to side of confinement cone 18. The opposite end of tube 16A would be in fluid communication with the pressurized air source. In the arrangement of FIG. 2, a notch 17 could be formed along the side of probe 14 in which tube 16A could matingly fit to keep it in a fixed orientation.

In one embodiment, notch 17 is 0.125 inch in diameter and approximately 3.5 inches long, and tube 16A is 0.063 inch outside diameter with no constriction at its distal end. Tube 14 is approximately 0.813 inches diameter and 4 inches long. Confinement cone 18 is approximately 0.750 inches at its widest diameter and extends approximately 0.250 inches from its connection to tube 14 to its lower most edge.

Further with regard to one embodiment, the lower distal end of tube 16A is positioned in abutment to or close to confinement cone 18 but approximately 0.070 inches above the plane of the lower edge of confinement cone 18. The system is designed to handle a maximum of approximately 40 psi air pressure. It has been found empirically with this arrangement that approximately 10 psi run time pressure is sufficient to induce substantially random, continuous tumbling of most single kernels.

FIG. 3 shows an additional degree of freedom of movement of probe 14. As indicated by arrow 54 in FIG. 3, probe 14 can be rotated around rotational axis 55 defined by arm 44. This could be by some sort of actuator or just manual translation of probe 14. Such tipping is not necessarily required, but facilitates easier cleaning of the end of probe head 14. FIG. 3 also illustrates one example of placement of detector 50 aligned with the outside edge of turntable 32, in the rotation path of metal sliver 52. A cable 51 would be connectable to the NIR device 20 or other controller.

As further indicated at FIG. 3, indicia or a ruler 19 can be integrated into tower 40 for user reference when positioning probe 14 in a vertical position relative to cup 12. Cup 12 would rotate in a horizontal plane.

Therefore, positioner 30 provides selected movement of probe 10 relative to a cup 12. It allows probe head 14 to be moved down into the open top of cup 12 such that confinement cone 18 enters partially down into cup 12, leaving some gap between its greatest diameter and the inside surface of cup 12 such that air jet 17 delivered by conduit 16 can effectuate tumbling of the kernel in cup 12.

FIG. 1 illustrates general proportionality between components for probe 10 and cup 12 for this exemplary embodiment. Cup 12 is approximately 2 cm by 2 cm. Its inner surface is basically a rotated parabola or partial ellipse. The widest diameter of kernel confinement cone is approximately 1.7 cm. Conduit 16 is approximately 6 cm long, as is probe head 14. As indicated in FIG. 2, probe head 14 would generate a light beam 8 (e.g. 25° cone) into a cup 12 when aligned underneath it. Light would also be collected with probe head 14.

The specific dimensions of these components can be selected and may vary depending on the circumstances, including the probe head used. And, again, different types of NIR analyzers can be used. It is the addition of components that promote optical interrogation from almost every orientation that is the improvement.

E. Operation

In operation, the system of FIG. 1-4 works as follows. Positioner 30 would be adjusted such that probe 14 would be vertically aligned above cup 12A (see FIG. 2). FIG. 4 illustrates how one detector 50 could be utilized and taken advantage of with a rotating turntable 32 in an automated operation. By attaching detector 50 near the side of turntable 32 and in alignment with the rotational path of metal sliver 52 the system could keep track of rotational position of turntable 32. Turntable 32 could have three indexed positions, namely, kernel interrogation or analysis position 61, kernel placement position 62, and kernel removal position 63. Drive 48 could be connected to an actuator under computer control to vertically raise probe 14 and lower probe 14. The computer or controller (could be associated with NIR device 20 or separate) could also be connected to an actuator that rotates turntable 32 between the three indexed positions.

To start an analysis of a kernel 2, the computer would vertically raise probe 14 by operation of slide drive 41 and turn turntable 32 by operation of motor 34 to move cup 12 to kernel placement position 62. Kernel 2 can be manually placed into cup 12 (or by automation, e.g., vacuum or pneumatic conveyance). The computer or controller could be programmed to turn turntable 32 such that cup 12 is rotated back to indexed position 61. Probe 14 would be automatically lowered into position in cup 12 and optical interrogation would proceed with tumbling of seed kernel 2 in cup 12. After optical interrogation (e.g. for a set period of time), the computer could by programmed to raise probe 14 and turn turntable 32 such that cup 12 is moved to the kernel removal cup position 63. The kernel would be removed (manually or automatically) to complete the test.

As can be appreciated, when cup 12A is rotated with a kernel to interrogation position 61, probe placement drive 48 could be operated to finely adjust the vertical position of probe 14 such that confinement cone 18 extends partially into cup 12A the precise amount desired (see FIG. 1).

NIR energy would be generated by NIR device 20 and directed along beam path 8 into cup 12 concurrently as air jet from end 17 of conduit 16 is directed into cup 12A. Selected transmitted or reflected NIR energy from and/or through tumbling kernel 2 would be collected by probe head 14. Generally a couple of seconds (or less) of collection of such reflectance and/or transmittance is sufficient for one kernel. The collected energy would be communicated to NIR device 20 for recordation. As stated, the collected energy over that time period, for the multiple orientations of the tumbling kernel 2, would be recorded and co-added to present an entire spectrum for that time period for the single kernel 2.

The single spectrum would then be analyzed by NIR device 20 and utilized to derive chemical components of interest for kernel 2 according to known spectroscopy procedures.

The origin (e.g. parentage) of kernel 2 of cup 12A is known and could be correlated to the spectrum derived from the foregoing procedure and stored for use in plant advancement experiments. This method allows for gathering optical interrogation of multiple orientations of the particle. The embodiment described above tumbles the particle. It attempts to bathe the particle in the electro-magnetic radiation from every angle. This tumbling imparts some randomness into the orientation relative to the electro-magnetic radiation. An average of the reflectance or transmittance of the radiation is taken. An estimate of the amount of oil, for example, in a kernel is derived from this average (e.g. 3% by total weight of the kernel).

As previously indicated, embodiment of FIGS. 1-4, cup 12 is coated with a diffusive and reflective coating. It initially was thought important to have a reflective and diffusive coating to collect the maximum amount of energy possible out of each interrogation. However, as previously mentioned, satisfactory results are obtainable without any coating, reflective or diffusive, relying on collection of reflectance from the particle under interrogation itself.

F. Options and Alternatives

It will be appreciated that the foregoing exemplary embodiment is given by way of illustration and example only and not by way of limitation. Variations obvious to those skilled in the art will be included within the invention.

For example, variations in materials, dimensions, operating parameters are possible. Some of these factors will be dependent upon the type of specimen being evaluated. The example above was relative a kernel of corn. The invention also has applicability to other agricultural seeds. One notable example is soybean seed. But still further, the invention has applicability to other particles. Examples include, but are not limited to, tablets, pellets or any similar object requiring quantitative measure for chemical components. For example, analysis of a pharmaceutical pill is possible.

Alternative methods of obtaining optical interrogation from different orientations are possible. The invention contemplates that interrogation from at least two different general planes of the particle are obtained. Preferably collection of transmittance or reflectance from a number of orientations is desirable, and from different locations on the particle. In other words, it is preferable that more than simply collection from a single plane of rotation of the particle be taken or from opposed surfaces in one plane of the particle.

Examples of obtaining different interrogation orientations could include some sort of vibration of the particle as opposed to using an air jet. There also could be some sort of mechanical finger or fingers that would knock or hit the kernel to change its orientation relative to a NIR beam. Still further, the kernel might be held in some mechanical gripper that is on some sort of gimple mount that can be turned to turn the particle in multiple orientations relative interrogation angle.

Collection of electro-magnetic energy can also vary. As discussed previously, collection could be through a detector separate from probe 14. Alternatively, both transmission and collection of NIR energy could be by probe 14. Furthermore, collection of light could be either solely from reflectance or transmittance from or through a moving kernel 2 or solely from collecting energy from a diffusive coating (without moving or tumbling kernel 2).

Still further, it is possible that kernel 2 could be fixed in position and a detector moved relative to the kernel to gather a plurality of optical interrogation orientations. Still further, a transmitter of electro-magnetic energy could be moved and/or the detector moved relative to the kernel. Finally, either transmitter or detector, or both, could be moved relative to kernel 2 and kernel 2 could be moved relative to transmitter and/or detector.

A single kernel of corn would be placed into cup 12A of FIG. 2. Optionally, a single kernel could be placed in cup 12B and another single kernel in cup 12C.

If multiple cups 12A-C of FIG. 2 are used, probe 14 could then be vertically raised by drive 48. Turntable 38 could be turned to align cup 12B with the vertical axis of probe 14, and probe 14 could then be moved back vertically downward by drive 48, the position indicated in FIG. 1. The procedure could be repeated for the new kernel 12 in cup 12B.

This process could optionally be repeated for a third separate kernel in cup 12C. Thereafter, a new set of three individual kernels could be replaced in each of cups 12A-C, and the process repeated individually for each of them, etc. Alternatively, once probe 14 is accurately aligned with one cup 12, a single kernel can be placed into that cup 12, optically interrogated, removed, and replaced with a new seed, etc. This would eliminate rotation of the turntable. Further, instead of tilting probe 14 back to insert and remove kernels, the turntable could simply be rotated from underneath probe 14 to place a kernel in or remove a kernel, and then rotated back into position.

Instead of rotating turntable 32 to position 61 for optical interrogation, probe 14 would be moved to each of positions 61, 62, or 63 and the interrogation take place accordingly.

Some additional options or alternatives are illustrated in FIGS. 5-7, again by way of example of, but not limitation to, variations on the invention.

Figure 5:
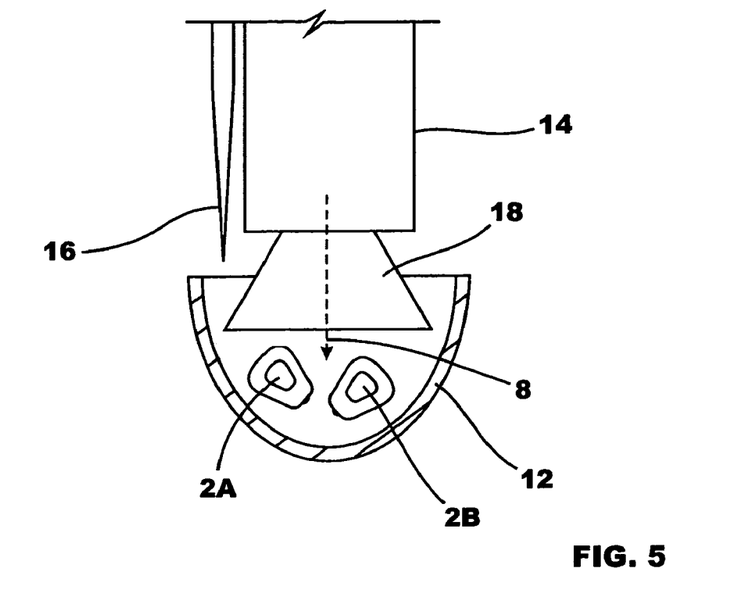
FIG. 5 is an enlarged diagrammatic view illustrating an optional sampling probe for simultaneous optical sampling of a plurality of particles.

FIG. 5 illustrates that more than one kernel could be interrogated at the same time. Two kernels, 2A and 2B, could be placed in a cup 12 and interrogated with an average of the energy collected by reflectance or transmittance from both kernels being recorded and/or averaged. It may be possible for even more than two kernels in one cup.

Figure 6:
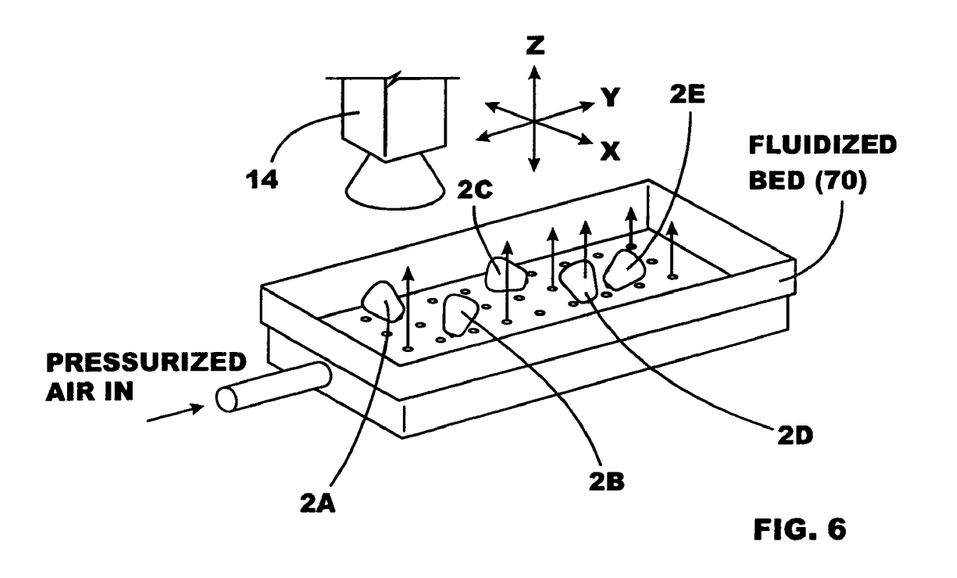
FIG. 6 is a diagrammatic perspective view of an alternative embodiment of optically sampling a plurality of particles.

FIG. 6 illustrates that one or more kernels could be tumbled relative to a probe 14 in a fluidized bed 70 to provide randomized different orientations of a kernel 2 to a detector 14.

Figure 7:
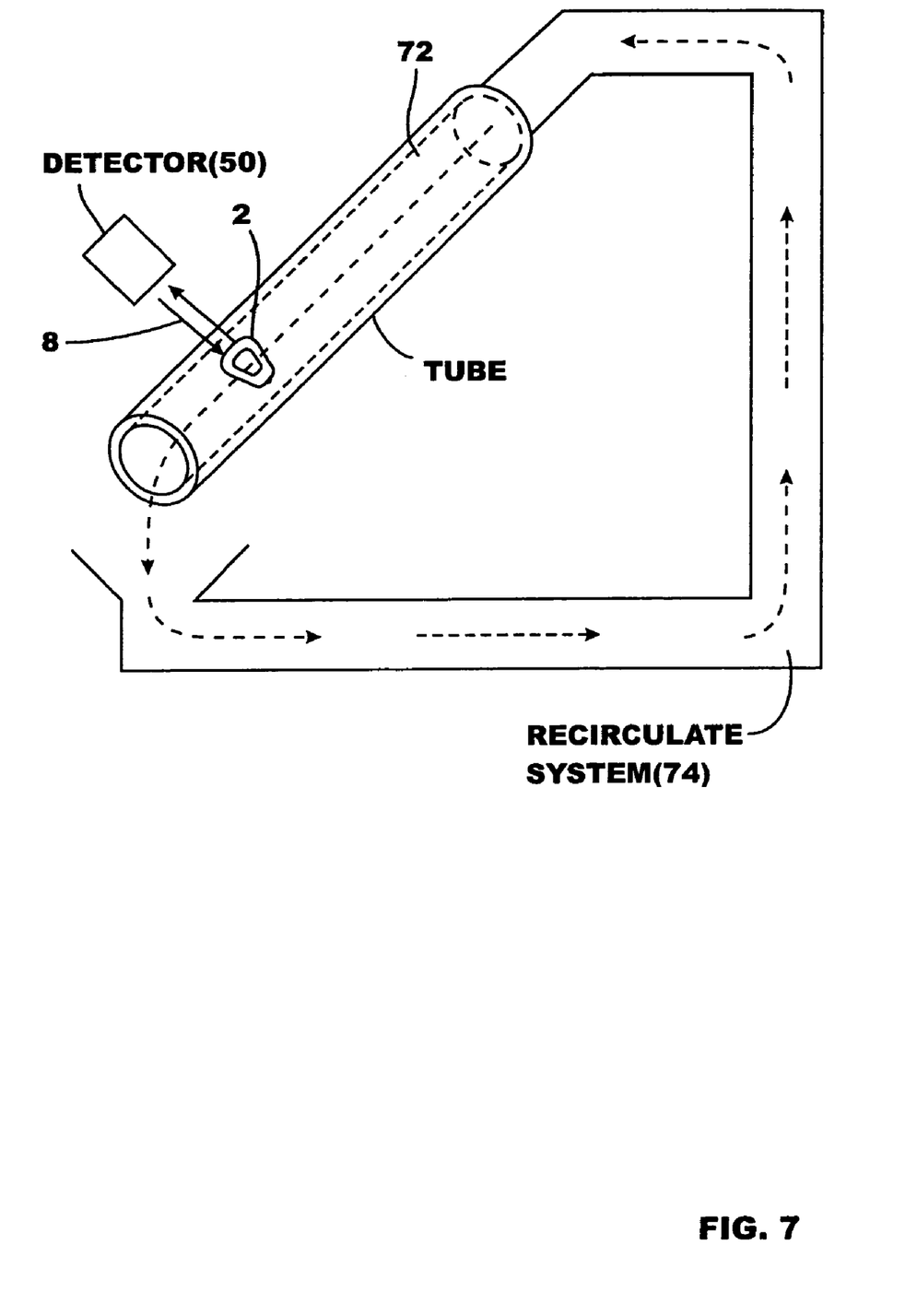
FIG. 7 is a highly simplified diagrammatic view of an alternative embodiment for repeated sampling of the same particle or particles by a recirculation system.

FIG. 7 illustrates that a single kernel 2 could be evaluated with a detector 50 picking up with reflectance or transmittance of NIR energy as it travels through tube 72. Different optical interrogation orientations could be obtained by then recirculating kernel 2 back into one end of tube 72 and pass it by detector 50 multiple times. A recirculation system 74 (e.g. pneumatic conveyance) could be adapted to statistically present kernel 2 in different orientations to detector 50 over a number of recirculated passes. This would also nondestructively allow gathering of optical interrogation from multiple orientations, and then averaging for a co-added single spectrum for kernel 2. Conversely, multiple kernels 2 could be sent by detector 50 and recirculated or multiple kernels sent serially by detector 50 in one pass by some sort of pneumatic conveying system.

As can be appreciated, by appropriate utilization of some sort of processor, programming can be created to automate operation of the system shown in FIGS. 1-4. Furthermore, a conveyance system could operate under control of such software and controller to, at appropriate times and in appropriate sequence, place a kernel into cup 12 at kernel placement position 62 of FIG. 4, be interrogated, and then be removed at kernel removal cup position 63 of FIG. 4.

The NIR analyzer can be programmed to evaluate each kernel according to set thresholds. One example would be to evaluate the absorption spectrum of a kernel according to amount of oil. If it is above a certain threshold it would be considered high oil. The conveyance system which removes the kernel from the cup at kernel removal position 63 could be instructed to send that kernel to a first bin. If evaluation of the kernel spectrum shows oil to be below a certain threshold, the system could convey it to a second bin. If the kernel is evaluated to have a medium oil content between the high and low thresholds, the conveyance system could send it to a third bin. Obviously, any number of different protocols are possible.

One method of optical interrogation utilizes NIR radiation. Other types of optical interrogation regimens may be used.

It can be seen that the foregoing exemplary embodiments in one or more of the stated objects, features, advantages, or aspects of the present invention. They each attempt to acquire optical interrogation from multiple directions for a single kernel, and in particular, from more than one plane of the kernel.

What is claimed is:

1. An apparatus for optical interrogation of a particle comprising:
   a. an optical interrogation probe adapted for optical interrogation orientation relative to a particle interrogation position;
   b. a pressurized jet adapted to vary the orientation of the particle relative to the optical interrogation orientation of the probe;
   c. so that the probe can obtain a plurality of optical interrogations of the particle from a plurality of orientations of the particle.

2. The apparatus of claim 1 further comprising a retainer defining a space and at least substantially surrounding the particle to prevent it from leaving the space.

3. The apparatus of claim 2 wherein the retainer comprises a cup shape.

4. The apparatus of claim 2 wherein the retainer includes one or more of a light reflective and light diffusive surface.

5. The apparatus of claim 1 wherein the pressurized jet comprises a pressurized gas or fluid source and nozzle adapted to create the pressurized jet.

6. The apparatus of claim 1 wherein the probe is adapted to collect near infrared electro-magnetic radiation.

7. The apparatus of claim 1 wherein the particle comprises an agricultural seed.

8. The apparatus of claim 7 wherein the agricultural seed comprises a single seed.

9. The apparatus of claim 7 wherein the agricultural seed comprises a corn seed.

10. The apparatus of claim 7 wherein the agricultural seed comprises a soybean seed.

11. The apparatus of claim 5 wherein the pressurized gas or fluid source comprises an air source.

12. A method for optical interrogation of a particle comprising:
    a. optically interrogating a particle from a plurality of orientations at least in multiple different planes by tumbling the particle relative to the optical interrogation with a pressurized jet;
    b. co-adding acquired optical interrogation into a single spectrum; and
    c. a analyzing the spectrum for chemical components or characteristics of the particle;
    d. to provide a quantitative measurement of one or more chemical components or characteristics of the particle;
    e. storing the quantitative measure of one or more chemical components or characteristics of the particle in a memory of an electronic device.

13. The method of claim 12 wherein the particle is an agricultural seed.

14. The method of claim 13 wherein the particle is a single agricultural seed.

15. The method of claim 13 wherein the particle is corn or soybean.

16. The method of claim 12 wherein the particle is a pharmaceutical pill.

17. The method of claim 12 wherein the optical interrogation comprises NIR electro-magnetic radiation.

18. The method of claim 12 wherein the plurality of orientations are substantially all orientations.

19. The method of claim 12 wherein the pressurized jet comprises an air jet.

20. The method of claim 12 further comprising placing a light diffusive surface near the particle during optical interrogation.

21. The method of claim 12 wherein the particle is interrogated within a fixed volume at least partially defined by a light reflective and diffusive surface.

22. The method of claim 12 wherein the pressurized jet comprises a gas or fluid jet.

23. A system for optically interrogating a particle comprising:
   a. an optical interrogation probe adapted for optical interrogation orientation relative to an interrogation position;
   b. a retainer adapted to retain a particle generally in the interrogation position;
   c. a pressurized jet adapted to vary the orientation of the particle relative to the optical interrogation orientation of the probe;
   d. an electrical connection between the probe and a processor;
   e. the processor adapted to receive and record reflectance or transmittance of optical interrogation of the particle from a plurality of orientations.

24. The system of claim 23 wherein the optical interrogation comprises NIR electro-magnetic radiation.

25. The system of claim 23 wherein the pressurized jet comprises a pressurized air source and air nozzle producing an air jet directed in the retainer to set up tumbling of particle in the retainer.

26. The system of claim 23 further comprising a light reflective and/or diffusive surface at or near the interrogation position.

27. The system of claim 23 wherein the processor is operatively connected to the pressurized jet and the probe.

28. The system of claim 23 wherein the particle comprises an agricultural seed.

29. The system of claim 28 wherein the agricultural seed comprises a single seed.

30. The system of claim 28 wherein the agricultural seed comprises a corn seed.

31. The system of claim 28 wherein the agricultural seed comprises a soybean seed.

32. The system of claim 23 wherein the pressurized jet comprises a pressurized gas or fluid jet.

33. The system of claim 32 wherein the gas or fluid comprises air.

34. A method for optical interrogation of a single agricultural seed comprising:
   a. optically interrogating a single agricultural seed from a plurality of orientations at least in multiple different planes while tumbling the single agricultural seed with a pressurized jet;
   b. co-adding acquired optical interrogation into a single spectrum; and
   c. analyzing the spectrum for chemical components or characteristics of the single agricultural seed;
   d. to provide a quantitative measurement of one or more chemical components or characteristics of the single agricultural seed;
   e. storing the quantitative measure of one or more chemical components or characteristics of the single agricultural seed in a memory of an electronic device.

35. The method of claim 34 wherein the single agricultural seed is a corn seed.

36. The method of claim 34 wherein the single agricultural seed is a soybean seed.

* * * * *